United States Patent
Kim

[19]

[11] Patent Number: 5,856,607
[45] Date of Patent: Jan. 5, 1999

[54] PROCESS FOR PRODUCTION OF ETHYLBENZENE FROME DILUTE ETHYLENE STREAMS

[75] Inventor: Dae K. Kim, Naperville, Ill.

[73] Assignee: Amoco Corporation, Chicago, Ill.

[21] Appl. No.: 850,198

[22] Filed: May 2, 1997

Related U.S. Application Data

[60] Provisional application No. 60/016,339 May 3, 1996.

[51] Int. Cl.$^6$ .................................. C07C 2/66; C07C 2/68
[52] U.S. Cl. ......................... 585/448; 585/314; 585/323; 585/463; 585/467
[58] Field of Search .................................... 585/314, 323, 585/448, 650, 655, 463, 467

[56] References Cited

U.S. PATENT DOCUMENTS

| | | | |
|---|---|---|---|
| 2,971,992 | 2/1961 | Bloch | 260/671 |
| 4,107,224 | 8/1978 | Dwyer | 260/671 |
| 4,524,230 | 6/1985 | Haensel | 585/467 |
| 4,832,920 | 5/1989 | Owen et al. | 422/190 |
| 5,013,334 | 5/1991 | Maurer | 55/26 |
| 5,138,113 | 8/1992 | Juguin et al. | 585/322 |
| 5,171,333 | 12/1992 | Maurer | 55/26 |
| 5,227,567 | 7/1993 | Mitariten et al. | 585/661 |
| 5,245,099 | 9/1993 | Mitariten | 585/650 |
| 5,365,011 | 11/1994 | Ramachandran et al. | 585/829 |
| 5,430,211 | 7/1995 | Pogue et al. | 585/323 |
| 5,502,971 | 4/1996 | McCarthy | 62/20 |

FOREIGN PATENT DOCUMENTS 655492  5/1994  European Pat. Off. .

OTHER PUBLICATIONS

Mortimer, Tim et al., "Processing Scheme Options for Ethylbenzene Production from dilute Ethylene Feedstocks", Sud–Chemie Group 1996 International Styromax Seminar, Sep. 24–26, 1996.

Fallon, Kevin J. et al., "The Mobil/Badger Dilute Ethylene to EB Process: Proven Technology for Low Cost Ethylbenzene", Sud–Chemie Group 1996 International Styromax Seminar, Sep. 24–26, 1996.

*Primary Examiner*—Glenn Caldarola
*Assistant Examiner*—Thuan D. Dang
*Attorney, Agent, or Firm*—Thomas E. Nemo; Mary Jo Kanady; Wallace L. Oliver

[57] ABSTRACT

The present invention relates to a process for the production of ethylbenzene from dilute ethylene streams, especially from mixtures of ethane and ethylene where such mixture is the offgas from a refinery operation, such as a fluid catalytic cracking (FCC) operation and wherein the unreacted ethane from the alkylation reactor is dehydrogenated to produce ethylene which is recycled into the original dilute ethylene stream.

34 Claims, 4 Drawing Sheets

PROCESS FOR PRODUCTION OF ETHYLBENZENE FROME DILUTE ETHYLENE STREAMS

This application claims the benefit of U.S. Provisional Application No. 60/016,339 filed May 3, 1996, which is incorporated herein by reference.

BACKGROUND OF THE INVENTION

The present invention relates to a process for the production of ethylbenzene from dilute ethylene streams, especially from mixtures of ethane and ethylene where such mixture is the offgas from a refinery operation, such as a fluid catalytic cracking (FCC) operation. The conventional processes for utilizing this type of stream for ethylbenzene production are generally focused on methods of utilizing only the "contained" ethylene. In particular, it has been difficult to upgrade the ethane component in the FCC offgas due to its dilute concentration coupled with the presence of olefinic materials in the mixture. The process of the present invention provides methods for not only converting the dilute ethane component to the more valuable ethylene but also for increasing the concentration of ethylene in the feedstream going to an alkylation reactor, thereby reducing the hydrocarbon throughput to the reactor and providing an efficient process overall. Ethylbenzene is useful for preparing styrene.

Ethylbenzene is usually prepared by the alkylation of benzene with ethylene. Commercial processes include liquid phase alkylation with Friedel-Crafts catalysts, such as aluminum chloride and phosphoric acid or zeolite catalyst, and vapor phase alkylation with acidic carrier catalysts, such as crystalline alumino-silicates. A disadvantage of these processes is that they require an essentially pure stream of ethylene. Typically, polymer grade ethylene is used to alkylate benzene in an alkylation reactor. Such polymer grade/pure ethylene is expensive to produce.

Ethylene is primarily obtained from the thermal cracking of saturated hydrocarbons, such as natural gas rich in ethane, propane and n- and iso-butane. Ethylene may also be obtained from the thermal or steam cracking of naphtha. A disadvantage of cracking is that other products are also produced, including diolefins and acetylene which must be separated from the ethylene, and such separations are costly and significantly increase the cost of producing ethylbenzene. Separation methods include extractive distillation and/or selective hydrogenation of the acetylene back to ethylene. Such separation methods may include cryogenic separation of ethylene from acetylene. A typical ethylene separation section of an ethylene plant utilizes a complex sequence of cryogenic and fractionation steps.

U.S. Pat. No. 5,138,113 discloses a two-step cracking-alkylation process for production of alkylaromatic hydrocarbons from natural gas containing mostly methane, the process comprising: 1) thermal cracking of the natural gas with formation of hydrogen and $C_2$–$C_3$ hydrocarbons, particularly, ethylene and acetylene; 2) separation of the $C_2$–$C_3$ hydrocarbons, particularly the ethylene and acetylene, by cooled adsorption in a solvent, and 3) conversion of the $C_2$–$C_3$ hydrocarbons from step (2) into alkylaromatics. This type of process leads to the production of alkylaromatic mixtures, primarily alkyltoluenes, which may be useful for premium gasoline blending but are not necessarily useful for preparing for a high purity chemical grade ethylbenzene as a single major product.

U.S. Pat. No. 4,524,230 discloses a method for preparing alkylaromatic compounds comprising a one-step cracking-alkylation process using a paraffinic hydrocarbon as a source of an alkylating agent. The process comprises cracking a paraffinic hydrocarbon into olefinic products on the surface of a non-acid catalyst comprising a metal from group VIII of the Periodic Table which may be supported on a nonacid-acting support in the presence of an aromatic compound. To prepare ethylbenzene, however, this process requires propane as a feedstock which must be decomposed on the surface of the catalyst to generate fragmented alkylating agent, i.e., ethylene. On the other hand, the FCC offgas usually contains only a minute amount of propane, and the process of the present invention does not require propane as an alkylating agent nor desire the fragmentation of propane or any other paraffins to occur during the alkylation reaction.

One method of reducing ethylene costs is to alkylate with dilute ethylene streams, which are available from most refinery FCC units. U.S. Pat. No. 4,107,224 discloses the vapor phase alkylation of benzene to ethylbenzene using a ZSM-5 zeolite as the catalyst. It is taught that the catalyst can handle feedstreams containing from abut 15 to about 20 weight percent ethylene while yielding an ethylbenzene purity of greater than 97 weight percent.

While this reference process shows that the contained ethylene can be alkylated in a vapor phase reactor using a zeolite catalyst, it does not teach conversion of the ethane component in a dilute ethylene stream. The diluents such as ethane and methane are used to control temperature of alkylation reactions, and then purged out for use as fuel.

U.S. Pat. No. 5,430,211 discloses a two-step process of preparing ethylbenzene or substituted ethylbenzenes. The process uses as raw materials, ethane and benzene or substituted benzene and comprises dehydrogenating ethane using a mordenite zeolite catalyst to produce a dilute stream of ethylene, and thereafter, alkylating benzene or substituted benzene with the dilute ethylene stream to yield ethylbenzene or substituted ethylbenzene. The dehydrogenation step comprises contacting an ethane feedstream with a catalytic amount of a dehydrogenation catalyst in a dehydrogenation zone under reaction conditions such that a dehydrogenation product stream containing predominantly ethylene and unreacted ethane is formed. The examples of ethane sources given are natural gas or naphtha. In the second step, the dehydrogenation product stream, with essentially no further purification or separation, and a benzene co-feed are contacted with a catalytic amount of an alkylation catalyst in an alkylation zone under reaction conditions such that ethylbenzene is produced. The catalytic dehydrogenation step is said to produce ethylene in high selectivity without the formation of unwanted impurities, such as acetylene and diolefins. The dehydrogenation product stream which contains predominantly unreacted ethane and a dilute concentration of ethylene can be fed without further purification or separation directly to the alkylation zone. The alkylation product stream is separated via fractional distillation, and unreacted ethane can be recycled to the dehydrogenation zone. It is stated that an advantage of the process is that it does not require a thermal cracker or expensive separation technologies. However, in order for this process to deliver a dilute ethylene stream from the dehydrogenation step without purification to the alkylation step, the conversion of ethane in the dehydrogenation step has to be kept relatively low to avoid formation of impurities such as propylene and xylenes. As a consequence, the concentrations of ethylene in the dilute ethylene stream generated are said to be as low as 5 weight percent and the amount of ethane to be recycled becomes correspondingly high; thus its usefulness for commercial application may be limited. Besides, the alkylation catalysts disclosed in this process do not consume ethylene completely and, therefore, an appreciable amount of unreacted ethylene will be recycled back to the dehydrogenation zone unless it is separated from ethane, which is a costly separation. The ethylene recycled to the dehydrogenation zone will reduce the life time of the dehydrogenation catalyst particularly in the absence of aromatic compounds in the ethane feedstream which may help to scavenge ethylene impurity.

U.S. Pat. No. 5,245,099, describes a method of using pressure swing adsorption technology to recover ethylene and heavier components from a hydrocarbon feedstream such as an FCC offgas for use in an ethylene plant. There is no disclosure of using a dilute ethylene/ethane stream to make ethylbenzene.

U.S. Pat. No. 5,365,011 describes a method of separating a gaseous alkene from a gaseous alkane by a pressure swing adsorption process unit alone or in combination with a distillation column wherein the alkene is preferentially adsorbed onto a bed of 4A zeolite at a temperature of abut 50° C. to about 200° C.,

SUMMARY OF THE INVENTION

The present invention relates to a process for preparing ethylbenzene comprising:

(a) contacting a first reactant mixture comprising ethylene and ethane with benzene in a reaction zone under reaction conditions where the benzene is alkylated by at least a portion of the ethylene to form ethylbenzene;

(b) removing from the reaction zone a second mixture comprising ethane that was present in the first reactant mixture;

(c) dehydrogenating at least a portion of the ethane in the second mixture to form ethylene;

(d) recycling to the reaction zone the ethylene formed by the dehydrogenation; and (e) recovering ethylbenzene from the reaction zone.

In the process of this invention, a mixture of ethane and ethylene, preferably where such mixture is the offgas from a refinery operation, such as a fluid catalytic cracking (FCC) operation, is used to alkylate benzene in an alkylation reactor to form ethylbenzene. During the alkylation reaction, at least a portion, and preferably most, of the ethylene is reacted with benzene to form ethylbenzene. The ethane, which is not reactive, is recovered from the alkylation reaction. This ethane is dehydrogenated to form ethylene, and the ethylene so formed is recycled to the alkylation reactor for conversion to ethylbenzene. Since it is not practical to dehydrogenate a mixture of ethylene and ethane, the process of this invention provides for a separation of the ethylene and ethane by the benzene alkylation reaction by reaction of the ethylene with benzene. The resulting ethane stream depleted in ethylene, can be readily dehydrogenated to form ethylene which can then be used for further alkylation. The process of this invention provides for an efficient use of all or most of the ethane and ethylene in a ethylene-containing feed stream, particularly a refinery offgas stream.

The present invention also relates to a process for preparing ethylbenzene from a dilute ethylene stream comprising:

(a) contacting a first reactant mixture comprising about 10 to about 30 wt. % ethylene and about 10 to about 30 wt. % ethane with benzene in a reaction zone under reaction conditions where the benzene is alkylated by at least a portion of the ethylene to form ethylbenzene;

(b) removing from the reaction zone a second mixture comprising ethane that was present in the first reactant mixture;

(c) dehydrogenating at least a portion of the ethane in the second mixture to form ethylene,;

(d) recycling to the reaction zone the ethylene formed by the dehydrogenation; and (e) recovering ethylbenzene from the reaction zone.

The present invention further relates to a process for producing ethylbenzene from a dilute ethylene stream from FCC offgas comprising light ends comprising hydrogen and methane and a heavy cut comprising ethylene, ethane, and $C_3+$ hydrocarbons, which comprises:

(a) separating the light ends from the heavy cut by passing the dilute ethylene stream from FCC offgas through a light ends removal unit and recovering an effluent stream comprising said light ends and another effluent stream containing said heavy cut;

(b) separating the $C_3+$ hydrocarbons by passing the effluent stream containing said heavy cut from the light ends removal unit through a heavy olefins removal unit under pressure and temperature conditions sufficient to separate substantially all of the $C_3+$ hydrocarbons and recovering an enriched ethylene effluent stream comprising ethylene and ethane;

(c) contacting the enriched ethylene effluent stream from the heavy olefins removal unit with benzene in a reaction zone under reaction conditions wherein the benzene is alkylated by at least a portion of the ethylene to form ethylbenzene and recovering the ethylbenzene;

(d) recovering from the reaction zone an alkylation reactor effluent stream comprising ethane;

(e) dehydrogenating at least a portion of the ethane in said alkylation reactor effluent stream to form an effluent stream containing ethylene; and (f) combining the ethylene-containing effluent stream thus formed with the dilute ethylene stream from FCC offgas going to the light ends removal unit thereby enriching the ethylene content of the FCC offgas stream and recycling to the reaction zone the ethylene formed by dehydrogenation.

The light ends removal may be accomplished by any means of separation which will separate light ends such as hydrogen, nitrogen and methane from ethane, ethylene, and heavier components of the FCC offgas stream, for example, a fractionation column using a refrigerant, such as a demethanizer column, an adsorption-desorption device such as a pressure swing adsorption (PSA) unit, or a membrane based separation unit. The use of pressure swing adsorption is preferred. Optionally, the hydrogen may be recovered and sold which provides enhanced value over using it as fuel gas.

A means for separating paraffins from olefins can be placed between the light ends removal unit and the heavy olefins removal unit to concentrate the ethylene further. The ethane separated can be sent to the cracker for dehydrogenation. Concentrating the stream in this manner would allow for a liquid phase alkylation reaction. The means for removing the ethane can be a fractionation column using a refrigerant, an adsorption-desorption device such as a pressure swing adsorption unit or a membrane-based separation unit. Also, it is possible to place the paraffin/olefin separation unit downstream of the heavy olefins removal unit.

A preferred embodiment of the present invention relates to a process for producing ethylbenzene from a dilute ethylene stream from FCC offgas containing a light ends component comprising hydrogen and methane and a heavy cut comprising ethylene, ethane, and $C_3+$ hydrocarbons, which process comprises:

(a) separating the light ends from the heavy cut by passing the dilute ethylene stream from FCC offgas to a pressure swing adsorption unit and contacting it with an adsorbent selective for the adsorption of said heavy cut under a pressure and temperature at which at least a portion of the heavy cut is adsorbed and recovering an effluent stream comprising said light ends and then desorbing said heavy cut from the adsorbent under reduced pressure and recovering another effluent stream containing said heavy cut;

(b) contacting the effluent stream containing the heavy cut with a deethanizer under a pressure and temperature sufficient to separate substantially all of the $C_3+$ hydrocarbons and recovering a dilute ethylene effluent stream comprising ethylene and ethane;

(c) contacting the dilute ethylene effluent stream from the deethanizer with benzene in a reaction zone under reaction conditions wherein the benzene is alkylated by at least a portion of the ethylene to form ethylbenzene and recovering the ethylbenzene;

(d) recovering from the reaction zone an alkylation reactor effluent stream comprising ethane;

(e) dehydrogenating at least a portion of the ethane in said alkylation reactor effluent stream to form an effluent stream containing ethylene, and (f) combining the ethylene-containing effluent stream thus formed with the dilute ethylene stream from FCC offgas going to the pressure swing adsorption unit thereby enriching the ethylene content of the FCC offgas stream and recycling to the reaction zone the ethylene formed by dehydrogenation.

The dehydrogenation of the ethane in the alkylation reactor effluent may be accomplished using catalytic dehydrogenation, but is preferably conducted in a steam cracker. The use of a steam cracker is efficient and provides a system having good longevity, and it additionally avoids the problems and expense associated with using dehydrogenation catalysts which may have a short life and require frequent downtime for removing spent catalyst and installing fresh catalyst. It is preferable that the cracking operation generates as much ethylene as possible from the ethane-containing paraffinic stream, and that one can achieve this by operating a steam cracker with steam to hydrocarbon feed weight ratio in the range of about 0.1 to about 1.0, preferably about 0.2 to about 0.5, and the cracking furnace tube outlet temperature in the range of about 600° to about 1100° C. preferably about 700° C. to about 900° C.

The present invention further relates to a process for producing ethylbenzene from a dilute ethylene stream from FCC offgas comprising hydrogen, methane, ethane, ethylene, and $C_3+$ hydrocarbons, said process comprising:

(a) subjecting said dilute ethylene stream to a cyclic adsorption process in at least one bed of adsorbent which selectively adsorbs ethylene, ethane, and $C_3+$ hydrocarbons, thereby producing a non-adsorbed hydrogen and methane component and an adsorbed ethylene, ethane, and $C_3+$ hydrocarbon component;

(b) removing the non-adsorbed hydrogen and methane component and, optionally, separating and recovering the hydrogen;

(c) desorbing the ethylene, ethane, and $C_3+$ hydrocarbon component and contacting it with a deethanizer under a pressure and temperature sufficient to separate substantially all of the $C_3+$ hydrocarbons and recovering a dilute ethylene effluent stream comprising ethylene and ethane;

(d) contacting the dilute ethylene effluent stream from the deethanizer with benzene in a reaction zone under reaction conditions wherein the benzene is alkylated by at least a portion of the ethylene to form ethylbenzene and recovering the ethylbenzene;

(e) recovering from the reaction zone an alkylation reactor effluent stream comprising ethane;

(f) dehydrogenating at least a portion of the ethane in said alkylation reactor effluent stream to form an effluent stream containing ethylene; and (g) combining the ethylene-containing effluent stream thus formed with the dilute ethylene stream from FCC offgas going to the bed of adsorbent in step (a) thereby enriching the ethylene content of the FCC offgas stream and recycling to the reaction zone the ethylene formed by dehydrogenation.

The present invention further relates to a process for producing ethylbenzene from a dilute ethylene stream from FCC offgas comprising hydrogen, methane, ethane, ethylene, and $C_3+$ hydrocarbons, said process comprising:

(a) passing the dilute ethylene stream into a pressure swing adsorption unit and (1) contacting the dilute ethylene stream with an adsorbent under pressure conditions whereby ethylene, ethane, and $C_3+$ hydrocarbons are selectively adsorbed while methane and hydrogen are separated, thereby producing a nonadsorbed hydrogen and methane component and an adsorbed ethylene, ethane, and $C_3+$ hydrocarbon component, and (2) reducing the pressure to desorb the ethylene, ethane, and; $C_3+$ hydrocarbon component from the adsorbent and passing it into a deethanizer;

(b) separating $C_3+$ hydrocarbons from the dilute ethylene stream under temperature and pressure conditions sufficient to separate substantially all of the $C_3+$ hydrocarbons and recovering an ethane- and ethylene-enriched effluent stream;

(c) contacting the ethane- and ethylene-enriched effluent stream with benzene in a reaction zone under reaction conditions wherein the benzene is alkylated by at least a portion of the ethylene to form ethylbenzene and recovering the ethylbenzene;

(d) recovering from the reaction zone an alkylation reactor effluent stream comprising ethane;

(e) dehydrogenating at least a portion of the ethane in said alkylation reactor effluent stream to form an effluent stream containing ethylene; and (f) combining the ethylene-containing effluent stream thus formed with the dilute ethylene stream from FCC offgas going to the pressure swing adsorption unit thereby enriching the ethylene content of the FCC offgas stream and recycling to the reaction zone the ethylene formed by dehydrogenation.

The separation of the $C_3+$ hydrocarbons in step (b) may be accomplished using a conventional distillation column operated at low temperatures or a sponge absorber equipped with a lean oil regeneration column. Benzene is a preferred sponge oil (or absorbent) but other hydrocarbon solvents such as light cat cycle oil used in an FCC vapor recovery unit can be used as the sponge oil.

The ethylbenzene thus formed is a valuable chemical product used for the manufacture of styrene. Styrene is used to make, for example, polystyrene.

The first reactant mixture in the process of this invention is a mixture comprising ethane and ethylene preferably wherein the ethane present is about 10 to about 50 wt. %, and the ethylene is about 10 to about 50 wt. %. It may also contain other components such as, for example, methane, hydrogen, nitrogen, carbon dioxide, and other low molecular weight hydrocarbons such as propane, propene, butenes and butanes. The first reactant mixture is a dilute ethylene stream that is available from a typical operation of a refinery's FCC vapor recovery unit after the removal or reduction to trace amounts of sour gases, such as hydrogen sulfide, carbonyl sulfur, carbon monoxide, and carbon dioxide, by well known methods such as amine treatment in order to facilitate downstream processing. A preferred source of this first reactant mixture is the offgas from a refinery's FCC operation. Such FCC units are well known to those of skill in the art. A typical FCC offgas may contain about 10 to about 30 wt. % (or about 5 to about 20 mole %) ethylene and about 10 to about 30 wt. % (or about 5 to about 20 mole %) ethane.

For the purpose of using the first reactant mixture in an alkylation reaction to produce high purity ethylbenzene it is desireable to purify the first reactant mixture to remove most, and preferably all, of the hydrocarbons containing three carbons or more since unremoved $C_3$ and $C_4$ olefins will form cumene ($C_9$) and $C_{10}$ aromatics which are difficult to separate from ethylbenzene. The alkylation of benzene with ethylene in the process of this invention can be conducted in a manner known to those of skill in the art. For example, it can be conducted by a liquid-phase, aluminum chloride catalyzed alkylation reaction or it can be by one or more gas or liquid-phase processes catalyzed by one or more acidic catalysts such as a zeolite catalyst. Methods for alkylating benzene with ethylene to form ethylbenzene are described, for example, in U.S. Pat. Nos. 4,107,224; 4,459,426; and 4,179,473, each of which is hereby incorporated by reference in its entirety.

The dehydrogenation of the ethane recovered after the alkylation reaction can be accomplished in a manner known to those of skill in the art. For example, the dehydrogenation can be accomplished catalytically over a suitable dehydrogenation catalyst; or, it can be accomplished thermally. Thermal steam cracking is the preferred method for converting the ethane to ethylene in the process of this invention.

DETAILED DESCRIPTION OF THE INVENTION

The offgas from a crude oil refinery's fluid catalytic cracking (FCC) operation typically contains about 15 mole percent ethylene and another 15 mole percent ethane. Hydrogen and methane constitute at least about 50% of the total FCC offgas volume, and may constitute about 50% to about 70% or more of the total FCC offgas volume. The conventional methods for utilizing this type of stream for ethylbenzene production focus only on the method that can afford alkylation of the "contained" ethylene. An example of such a conventional process is described in Fallon, K. J.; Wang, H. K. H.; and Venkat, C. R., "U.K. Refinery Demonstrates Ethylbenzene Process," Oil & Gas Journal, Apr. 17, 1995 which is incorporated herein by reference in its entirety. The process of this invention produces additional ethylene by means of cracking or dehydrogenation of the ethane in the FCC gas thereby utilizing much more of the available two-carbon hydrocarbon materials. The FCC offgas used in the process of the present invention is preferably FCC offgas which has been treated by methods well known to those in the art to remove acid or sour gases such as $CO_2$ and $H_2S$, generally by scrubbing in a caustic wash or by a regenerable amine system within the refinery. Other impurities, such as ammonia and nitriles typically are removed in a water wash, and acetylene is typically removed by catalytic hydrogenation. Such pretreatments may take place in the refinery.

After removal of sour gases and other such contaminants, the FCC offgas, which typically comprises hydrogen, carbon monoxide, nitrogen, methane, ethylene, ethane, and heavier components such as propylene, propane, butenes, butane, and pentenes and pentanes is sent to a light ends removal unit, preferably a PSA unit, to remove methane and hydrogen.

Ethylene, ethane, and C3+ components are then sent on to a deethanizer where the C3+ components are removed. The resulting ethylene/ethane stream which also contains some hydrogen and methane is sent to the alkylation reactor where the ethylene is reacted with benzene to form ethylbenzene. The vent gas from the alkylation reactor, which is primarily ethane, is sent to a thermal cracker to be dehydrogenated and converted to ethylene. This conversion of ethane to ethylene provides an enhanced value over the typical process in which the ethane along with hydrogen, methane and other gases which do not react in the alkylation reactor are burned as fuel. Following dehydrogenation, the stream from the steam cracker which contains ethylene, ethane, methane, hydrogen, and heavy pyrolysis products, such as benzene, may be washed to remove $C_5$+ heavier components and then is combined with the FCC offgas stream being fed to the pressure swing adsorption unit for removal of light ends. Thus the value of the unreacted ethane in the dilute ethylene/ethane stream is enhanced by converting the ethane to ethylene which can be used to produce ethylbenzene rather than burning it as fuel. This process affords increased ethylbenzene production capacity. Approximately 40% to 80% and preferably about 50% to about 75% of the ethane in the feed going to the steam cracker is converted to ethylene on a once through basis with some production of methane, hydrogen and $C_3$ and heavier by-products. In the present invention employing recycle to the steam cracker, substantially all of the ethane is converted to ethylene. The steam cracker may also receive ethane from an external source, such as those commercially available in high purity or as a mixture with propane, in addition to the vent gas from the alkylation reactor.

It is not easy, nor practical to crack or dehydrogenate ethane where ethylene and/or other olefins are present. Thus, the refinery is not a likely place to enhance the ethylene content of a mixed stream of ethylene and ethane. While an olefins plant has a cold section that can separate olefins, the logistics, capacity, and cost of the separation makes it difficult to process a dilute ethylene stream from outside for ethylbenzene (EB) production.

In this invention, an ethylbenzene alkylation reactor itself is used as an efficient scavenger of olefins. The gaseous effluent stream, i.e., the purge/tail gas stream from the alkylation reactor, is rich in ethane and paraffinics, thus suitable for dehydrogenating to ethylene. The non-reactive components such as hydrogen and methane that do not participate in either alkylation reactions or cracking reactions are eventually purged from the stream and, in doing so, have the effect of concentrating the ethylene further. By using the process disclosed herein, hydrocarbon value is approximately doubled. In the process of this invention, an offgas stream containing ethylene and ethane from an oil refinery can be used to prepare ethylbenzene, i.e., a stream that was not specifically prepared by the dehydrogenation of ethane.

A demethanizer unit can be used to separate out the light ends. A demethanizer column using a refrigerant under pressure has the advantage of providing a sharp separation between methane and ethylene; however, it has the disadvantage of being more costly than the pressure swing adsorption unit. Typically in the demethanizer the methane, hydrogen, and other light ends are separated from the $C_2+$ components of the feedstream at about −75° C. to about −120° C., preferably at about −100° C. using a pressure of about 14 to about 42 kg/cm$^2$ (about 200 psia to about 600 psia), preferably about 21 to about 35 kg/cm$^2$ (about 300 psia to about 500 psia), A disadvantage of processes which require polymer grade ethylene for the preparation of ethylbenzene is that the processes of separating the ethylene using removal of light ends with a demethanizer followed by a series of cryogenic separation steps to prepare a $C_2$ fraction and then split ethylene from ethane requires a high capital expenditure and the increase in pressure and reduction in temperatures needed to operate such systems requires a significant consumption of energy which adds to the cost of the system.

It has been surprisingly and unexpectedly discovered that the benzene alkylation reactor can be operated using an ethylene/ethane feedstream which is somewhat less pure than that obtained using cryogenic distillation in a demethanizer and that one can still obtain good commercial quantities of ethylbenzene using a simpler and less expensive means of removing light ends, such as a pressure swing adsorption (PSA) unit which can be used to purge the methane and hydrogen so that they do not build up in the feedstream. This process affords a simpler and less expensive method of removing light ends which may provide a commercial advantage over methods which require more severe conditions for separation and are more complicated and more expensive to operate. Use of PSA in the present invention provides a method of concentration and recovery of ethylene and the heavier $C_3+$ components from FCC offgas without expensive cryogenic separation steps to remove the lighter components, as well as a method of concentration and recovery of ethylene that is produced by recycling ethane not consumed in the alkylation reactor and converting it to ethylene which may be combined with the FCC offgas and again enriched by removing light ends using PSA.

The removal of the light ends, such as hydrogen, methane, nitrogen, etc., is preferably accomplished through use of a pressure swing adsorption (PSA) unit, which is an adsorption-desorption unit in which the hydrogen, methane, and other light ends are adsorbed under pressure onto a suitable adsorbent material. Suitable adsorbent materials include an suitable adsorbent material having a selectivity for various components of a feedstream over other such components, thereby providing a less readily adsorbable component and a more readily adsorbable component. Suitable adsorbents include, but are not limited to, activated carbons, molecular sieves, charcoal, activated clays, silica gels, activated aluminas and the like. The molecular sieves may include, for example silicoaluminoposphates and aluminophosphates and zeolitic molecular sieves. The pressure swing adsorption unit typically contains at least one bed of adsorbent and preferably contains about three to about ten or more adsorbent beds. The use of a PSA unit to remove light ends has the advantages of requiring less severe conditions and being more cost effective than cryogenic separation methods which require extremely low temperatures and high pressures and which are very expensive to operate.

Pressure swing adsorption (PSA) provides an efficient and economical means for separating a multi-component gas stream containing at least two gasses having different adsorption characteristics. In pressure swing adsorption, a multi component gas is typically fed to at least one of a plurality of adsorption zones at an elevated pressure effective to adsorb at least one component, while at least one other component which is less strongly adsorbed passes through. At a defined time, the feedstream to each bed of an adsorption zone is terminated and each adsorption bed undergoes a series of cyclic operating steps comprised of one or more depressurizations or blowdowns, desorption of the more strongly adsorbed components at low pressure, pressure equalization to conserve energy, purging of the bed, and finally repressurization to begin another cycle. *Pressure Swing Adsorption* by D. M. Ruthven, S. Farooq, K. S. Knaebel, VCH Publishers, Inc., 1994, incorporated herein by reference in its entirety, describes Pressure Swing Adsorption technology. In addition, U.S. Pat. No. 5,245,099, incorporated herein by reference in its entirety, describes one method of using pressure swing adsorption technology to recover ethylene; U.S. Pat. No. 5,365,011, incorporated herein by reference in its entirety, describes a method of using pressure swing adsorption technology to separate a gaseous alkene from a gas mixture comprised of the alkene and one or more alkanes; and EP 0 655 492, incorporated herein by reference in its entirety, describes a method of recovering an alkene from a cracked hydrocarbon stream using a cyclic adsorption process. Details of the construction and operation of pressure swing adsorption systems, including single and multiple beds are disclosed, for example, in U.S. Pat. No. 2,944,627 incorporated herein by reference in its entirety.

Various classes of adsorbents are known to be suitable for use in PSA systems, the selection of which is dependent upon the feedstream components and other factors generally known to those skilled in the art. In general, suitable adsorbents include, but are not limited to, molecular sieves, silica gel, activated carbon and activated alumina.

The PSA unit of the present invention is designed to make a split between $C_1$ and $C_2+$ hydrocarbons. The adsorption zone pressure ranges from about 3.5 kg/cm$^2$ to abut 28 kg/cm$^2$ (about 50 to about 400 psia), preferably from about 5 kg/cm$^2$ to about 200 kg/cm$^2$ (about 70 to about 200 psia). The adsorption zone temperature is typically in the range of about 0° C. to about 200° C. and preferably from of about 30° C. to about 70° C. The desorption pressure (i.e., the pressure at which the desorption effluent is recovered) is in the range of about atmospheric pressure to about 7 kg/cm$^2$ absolute (about 100 psia), preferably from about atmospheric pressure to about 5 kg/cm$^2$ absolute (about 70 psia). The amount of ethane and ethylene recovered as the low pressure product is in the range of about 50 to abut 95 mole percent of the ethane and ethylene in the feedstream, preferably from about 80 to about 98 mole percent. The hydrogen, methane, nitrogen, and other light ends recovered from the PSA unit may be used as fuel gas, or more preferably, may be further processed to recover high purity hydrogen, preferably by using another PSA unit designed to make a split between hydrogen and methane.

The deethanizer for removing propylene and other $C_3+$ olefins and hydrocarbons can be a conventional distillation column operating at low temperatures or a sponge absorber equipped with a lean oil regeneration column. Benzene is a preferred sponge oil (or absorbent), but other hydrocarbon solvents such as a light cat cycle oil used in an FCC vapor recovery unit can be used as the sponge oil. The cryogenic deethanizer is preferred to the sponge absorber in the present invention. The deethanizer is operated at a pressure in the range of about 7 to about 35 kg/cm$^2$ absolute (about 100 to about 500 psia), preferably about 10 to 19 kg/cm² absolute (about 140 to about 260 psia). The temperature of the feed gas to the deethanizer will be in the range of about −20° to about −70° C. and preferably around −45° C., such that most of the $C_3$ and essentially all of the heavier materials will be removed as bottoms. In one embodiment of this invention, an acetylene hydrogenation reactor and also additional separation equipment such as refrigerated flash drum may be placed the downstream of the heavy olefins removal unit so that the overhead stream containing $C_2$ and lighter materials is passed through and treated to further reduce the light ends content. The light ends thus removed may then be recycled to the light ends removal unit.

Following separation of the $C_3+$ olefins, the ethane-ethylene stream which now contains only minute amounts of $C_3+$ olefins is fed to an alkylation reactor along with a benzene stream, in a benzene to ethylene mole ratio of about 2:1 to about 8:1. The alkylation reactor can be any of the fixed bed reactors using a zeolite catalyst or simply the classical aluminum chloride catalyzed liquid-phase EB process known to those of skill in the art. The fixed bed reactors may be operated in a liquid or vapor phase or a mixed phase, and, depending on the mode of operation, the specific operating conditions can vary widely. In general, the alkylation in fixed beds is effected at a pressure in the order of about 10 to about 50 kg/cm² absolute (140 to 700 psia) and at temperatures of from about 150° to about 430° C. The conditions for effecting such alkylation and transalkylation are generally known to those skilled in the art. In all types of alkylation reactors, the ethylene is essentially completely consumed by reaction, and the ethane, and any methane and hydrogen present, are usually considered to be inerts that do not participate in the alkylation reaction and, therefore, are to be purged out of the alkylation section.

Following the alkylation of the benzene, the condensable product mixture may be separated in a series of distillation columns by standard techniques and the high purity ethylbenzene may be recovered. Other alkylated hydrocarbons such as di-and triethylbenzenes that are separated during distillation may be further subjected to transalkylation reactions with benzene to yield more ethylbenzene. The unreacted ethane may be separated from the condensable product mixture stream in a suitable gas/liquid separation device and can be recycled to a dehydrogenation reactor and converted to ethylene which can then be recycled into the dilute ethylene stream from FCC offgas or other source and back to the alkylation reactor.

The unreacted light paraffinic purge/tail gas stream, from the alkylation reactor, which is rich in ethane and paraffinics, is subjected to a dehydrogenation operation to convert the ethane to ethylene. The dehydrogenation is preferably carried out in a thermal cracker; however, a catalytic reactor may also be used. Thermal cracking using a steam cracking furnace is the preferred method for dehydrogenating ethane to produce ethylene in the process of the present invention. The ethane-rich purge/tail gas stream is introduced to a cracking furnace at a pressure of from about 2 to about 10 kg/cm² absolute (about 30 psia to about 140 psia), preferably from about 3 to about 6 kg/cm² absolute (about 43 psia to about 85 psia), and steam is added to the furnace tube at a steam to hydrocarbon feed weight ratio in the range of about 0.2 to about 1.0, and the tube outlet temperature is maintained in the range of about 700° C. to about 1000° C. to achieve as much ethylene as possible from the ethane-containing paraffinic stream from the alkylation unit.

DESCRIPTION OF THE PREFERRED EMBODIMENTS AND DETAILED DESCRIPTION OF THE DRAWINGS

Example 1

Figure 1:
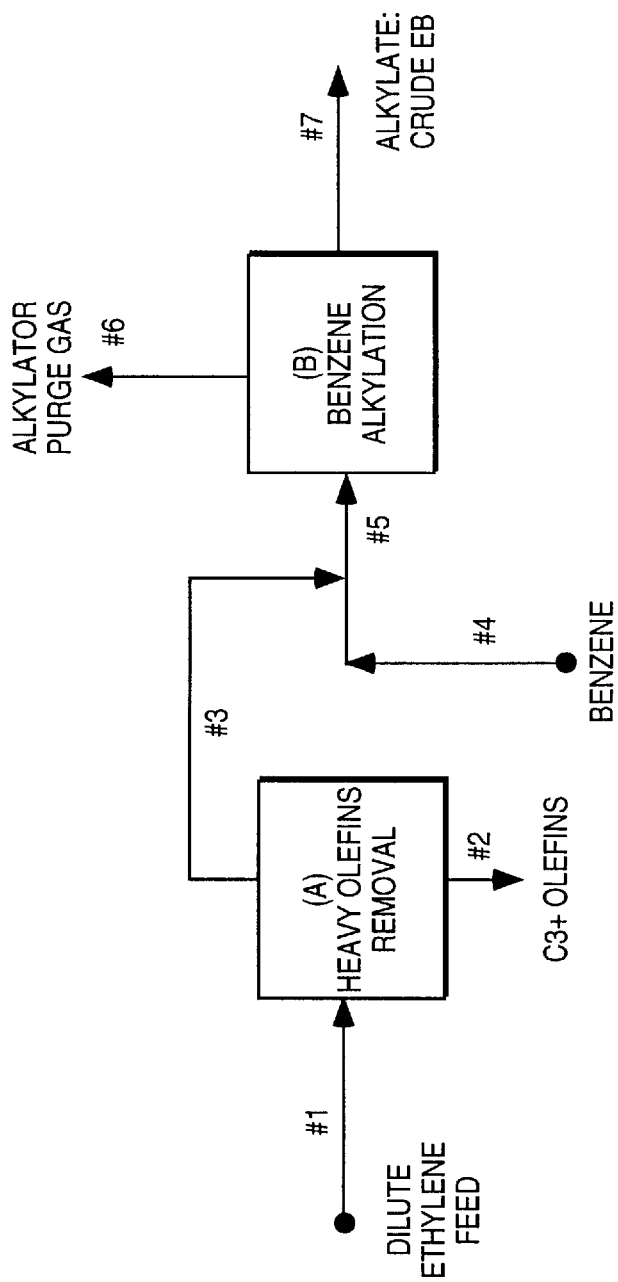
FIG. 1 illustrates a method for utilizing a dilute ethylene stream for ethylbenzene production which does not include the dehydrogenation step.

One method for utilizing a dilute ethylene stream for ethylbenzene production is depicted in a simplified diagram as shown in FIG. 1. The flow rates and concentrations of the various streams are given in Table I below. This embodiment describes preferred process steps, but does not include the dehydrogenation step. Stream 1 is a dilute ethylene feed stream that is available from a typical operation of a refinery's FCC vapor recovery unit after removing sulfur and most of $CO_2$ via, for example, an amine treatment. It may contain about 16.4 mole percent ethylene and about equal amount of ethane as indicated in Table I.

The feed stream also contains about 2.2 mole percent propylene and smaller amounts of $C_4$ olefins. The $C_3$ and heavier olefins are removed to trace levels (less than 0.05 wt %) in Facility A (heavy olefins removal) before the ethylene stream is routed via line #3 to the benzene alkylation section designated as B. Otherwise, the $C_3$ and $C_4$ olefins would be alkylated with benzene to form $C_9$ and $C_{10}$ aromatic hydrocarbons, which not only consume benzene but may be difficult to separate from ethylbenzene by distillation to meet a high purity (99.7+%) requirement for EB product. Cumene ($C_9$) is more difficult to separate than $C_{10}$ aromatics. For these reasons, it is desirable to limit the combined concentration of propylene and $C_4$ olefins in the ethylene stream to about 1000 ppmwt based on ethylene content.

The facility A for removing $C_3+$ olefins could be a conventional distillation column operating at low temperatures (i.e., a deethanizer) or a sponge absorber equipped with a lean oil regeneration column. Benzene is a preferred sponge oil (or absorbent), but other hydrocarbon solvents such as a light cat cycle oil used in an FCC vapor recovery unit can be used as the sponge oil. A deethanizer column is very effective for obtaining a sharp separation between $C_2$ (ethylene, ethane) and C3+ hydrocarbons. For the purpose of this embodiment, about 2 wt. % of ethylene is lost to the $C_3+$ olefin stream 2, i.e., ethylene recovery from Facility A is taken as 98 wt. % when $C_3+$ olefins are substantially removed in a sponge absorber or other heavy olefins removal unit in Facility A. If the refinery does a more efficient job of removing $C_3+$ olefins before sending the dilute ethylene stream for use in a chemical plant, the sponge absorber or other heavy olefins removal facility, may not be needed.

The ethylene stream 3 with only minute amounts of $C_3+$ olefins is fed to an alkylation reactor along with the benzene stream 4 in a benzene to ethylene mole ratio of about 2:1 to about 8:1. The alkylation reactor could be any of the fixed bed reactors using a zeolite catalyst or simply the classical aluminum chloride catalyzed liquid-phase EB process known to those of skill in the art.

The benzene alkylation unit represented by B consists of at least an alkylation reactor and a benzene recovery column. The alkylate, i.e., a crude ethylbenzene product in stream #7, is distilled out through the bottoms of the benzene recovery column, and then subjected to further refining, typically by distillation, to recover a high purity ethylbenzene. Integration of a transalkylation reactor into an EB process, in order to optimize EB production from the polyethylbenzenes formed in the alkylation reactor, is useful.

The ethylene and other olefin components that may be present are usually consumed completely in the alkylation reactor. However, the hydrogen and light paraffinic hydrocarbons such as methane and ethane contained in the dilute ethylene feed stream do not participate in the alkylation reactions and, therefore, are purged out of the alkylation system either from the alkylation reactor or from the overhead of the benzene recovery column. The purged gas in stream #6 is also called tail gas.

Table I gives an example of the quantities of materials for the process described in the above as calculated according to standard engineering practices. For example, a dilute ethylene stream that can be derived from a large scale fluid catalytic cracking unit has a total flow rate of 54,330 lb/hr or 25.8 million standard cubic feet (SCF measured at 60° F. and 1 atm.) per day (MMSCFD) with the weight and mole percent compositions as listed in Table I.

After the $C_3$+ heavy olefins are substantially removed along with a 2 wt. % of ethylene loss to stream 2, the ethylene available for alkylation of benzene to ethylbenzene is 12,740 lb/hr which is equivalent to 98 wt. % of the feed ethylene content of stream 1. The ethylene concentration in stream 3 (16.8 mole percent) is hardly changed from that of feed stream 1.

The ethylbenzene produced in the alkylation section is 47,748 lb/hr or 418 Mmlb/yr. This is calculated by multiplying the ethylene component flow rate, 12,740 lb/hr, of the alkylator feed stream 3 with the molecular weight ratio of EB to ethylene (106/28) since ethylene is completely consumed during the benzene alkylation, and again multiplying by a factor of 0.99 to account for about 1 wt. % heavy by-product formation.

The purge gas form the alkylation section is about 66% by weight of the total dilute ethylene feed stream 1, and about 80% by volume.

Example 2

Figure 2:
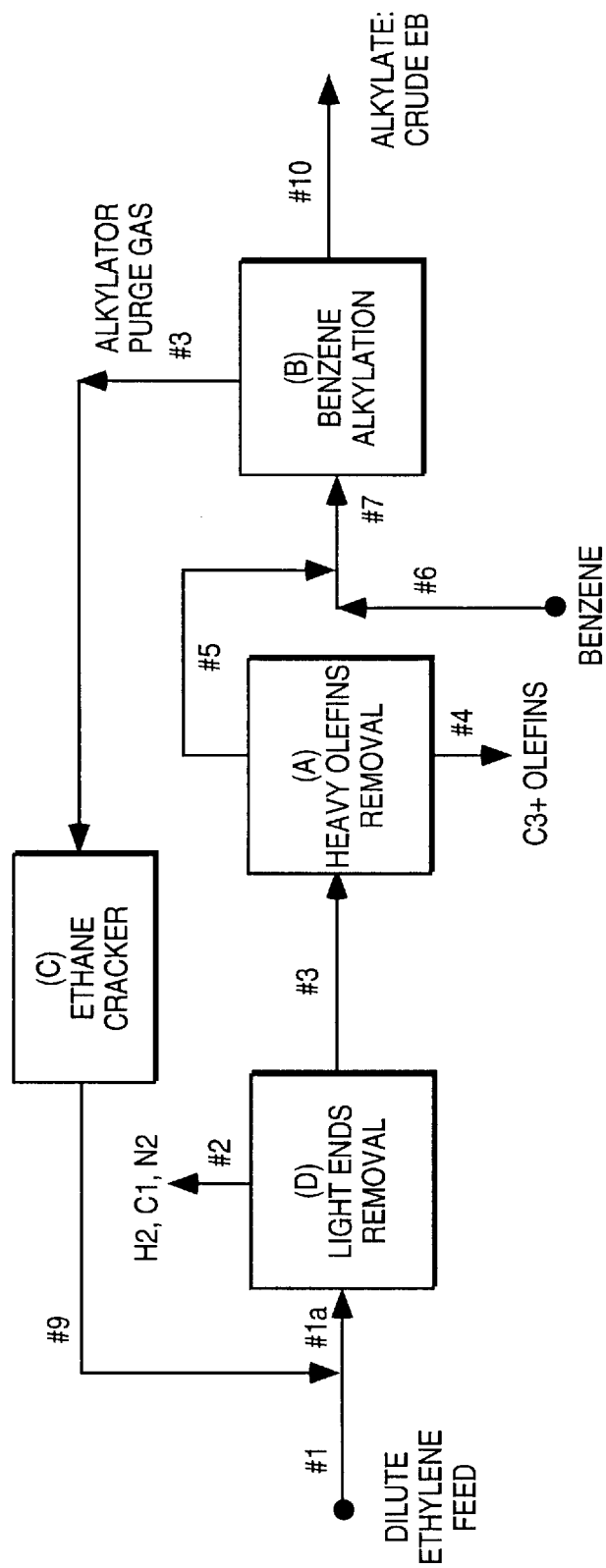
FIG. 2 illustrates an embodiment of the present invention in which the unreacted light paraffinic purge gas stream #8 from the benzene alkylation reactor (B), which is rich in ethane, is subjected to a dehydrogenation operation in a dehydrogenation facility (C) and the resulting ethylene-rich gaseous hydrocarbon effluent (stream #9) is combined with the dilute ethylene feed stream #1 going to the light ends removal facility (D) which in FIG. 2 is a demethanizer column.

A preferred embodiment of the present invention is schematically illustrated in FIG. 2, and the quantities of materials are presented in Table II.

The dilute ethylene feed stream 1 from an FCC refinery unit is identical to that of Example 1 in both volume and composition. Also, the $C_3$+ olefins contained in the dilute ethylene stream (#3) are substantially reduced in the heavy olefins removal facility A in the same manner and efficiency as described in Example 1, except for the unit capacity and size which are expected to be smaller than those of Example I because of the reduced flow rate of the stream #3 due to the use of a light ends removal facility D which is described below. The effluent stream #5 from the heavy olefins removal facility A is combined with the benzene feed stream #6 and fed to the benzene alkylation unit B. The alkylated product stream #10 is then treated in the same manner as in Example 1 to recover ethylbenzene product.

In this example of the invention, as shown in FIG. 2, the unreacted light paraffinic purge gas stream 8 from the alkylation section, which is rich in ethane, is subjected to a dehydrogenation operation in a suitable facility C. The resulting ethylene-rich gaseous hydrocarbon effluent (stream 9) is combined with the dilute ethylene feed stream 1. Stream 9 may, if necessary, be treated to remove components other than ethylene and ethane.

The dehydrogenation operation can be carried out in a thermal cracker or a catalytic reactor. Thermal cracking using a steam cracking furnace is the preferred method for dehydrogenating ethane to ethylene in the process of this invention. The ethane-rich purge/tail gas stream 8 is introduced to a multitube cracking furnace at approximately 45 psia (about 3.2 kg/cm$^2$ absolute), and steam is added to the furnace tube at a ratio of 0.3 lb/lb of hydrocarbon feed. The tube outlet temperature is adjusted at 1565° F. (852° C.) to achieve 70 wt. % conversion of ethane with an ethylene selectivity of 73.3 wt. % on a once-through basis.

The effluent from the furnace is cooled to approximately 250° F. (121° C.) in transfer line exchangers (TLE) while generating high pressure steam. The cooled hydrocarbon effluent from the TLE contains approximately 5 wt. % condensable $C_6$ and heavier pyrolysis gasoline components, and about 0.5 wt. % acetylene compounds. The $C_6$+ liquid hydrocarbons can readily be stripped by a simple water wash, and the acetylene compounds are hydrogenated to ethylene by conventional catalytic means known to those of skill in the art. The water wash and the acetylene hydrogenation steps may be considered as an integral part of the cracker unit represented by C. The cracker unit C, however, need not include the ordinary cryogenic separation equipment generally employed in olefin plants.

It is preferable that the cracking operation generates as much ethylene as possible from the ethane-containing paraffinic stream 8, and that one can achieve this by operating a steam cracker with steam to hydrocarbon feed weight ratio in the range of about 0.2 to about 1.0, and the furnace tube outlet temperature in the range of about 1300° to about 1700° F. (about 700° to about 925° C.).

The cracker effluent stream 9 prepared as described above is rich in ethylene, but it also contains increased amounts of methane and hydrogen as a result of the cracking operation. Some of these light ends are preferably removed before the stream is recycled to the alkylation section; otherwise, the light ends comprising methane and hydrogen which are not consumed by the alkylation reactions will accumulate in the system. One may install a light ends removal facility D for the stream 9 alone. But, since the dilute ethylene feed stream 1 also contains a substantial amount of light ends, it is preferable to have the light ends removal facility D remove light ends from the combined streams, i.e., stream 1$a$.

The light ends removal facility D could be a fractionation column using a refrigerant (i. e., a demethanizer), an adsorption-desorption device such as a pressure swing adsorption (PSA) unit, or a membrane based separation unit. In Example 2, a demethanizer column is used, whereas a PSA unit will be used in Example 3 for removing the light ends.

A demethanizer column using, for instance, a −150° F. (−101° C.) refrigerant at 450 psig (31.6 kg/cm$^2$ gauge) is very effective for obtaining a sharp separation between methane and ethylene. For this example, the demethanizer removes 99% of methane and hydrogen contained in the combined stream 1$a$, while 2% of ethylene is to be lost to stream 2, although the demethanizer is capable of achieving much better separation. The light ends removed from D, i.e., stream 2, may be used as fuel.

Table II shows the material balance for the invention process embodied in Example 2 as calculated according to standard engineering practices. The steam cracker is operated to give 70% ethane conversion with 73.3 wt. % ethylene selectivity. The yields of various cracking products can be seen by comparing the cracker feed stream 8 with product stream 9. For the purpose of simplicity of calculation, the $C_6+$ heavy hydrocarbon liquid generated during the cracking is lumped as $C_5+$ in stream 9 as if the $C_6+$ liquid is not stripped from the cracker effluent by water wash. As a consequence, the heavy olefins stream 4 shows an unusually large amount of $C_5+$, as if $C_5+$ is being removed with heavy olefins. In operation, $C_6+$ heavy liquids are removed from the cracker effluent, not from the heavy olefins removal facility.

The benefits of this embodiment are evident when the ethylene stream 5 fed to the alkylation reactor of this example is compared with that of Example 1 (stream 3). The comparison is summarized in Table A below.

TABLE A

Comparison of Benefits

|  | Example 1 | Example 2 |
|---|---|---|
| Dilute Ethylene Feed |  |  |
| Ethylene content (lb/hr) | 13,000 | 13,000 |
| Total vol. flow (MMSCFD*) | 25.8 | 25.8 |
| Alkylation Reactor Feed Gas |  |  |
| Total gas flow (MMSCFD) | 24.7 | 13.2 |
| Ethylene conc. (Mole %) | 16.8 | 53.8 |
| Ethylene flow (lb/hr) | 12,740 | 21,888 |
| Ethylene yield on Feed $C_2=$ | 98.0% | 168.4% |
| Ethylbenzene Production (lb/hr) | 47,748 | 82,034 |
| Relative production rate | 1.0 | 1.72 |

*MMSCFD = Million Standard Cubic Feet Per Day

In utilizing the identical dilute ethylene feed stream, the process of Example 2 results in a much smaller volumetric flow or throughput to the alkylation reactor with a substantially higher ethylene concentration than the process of Example 1. This would mean a more efficient design for the alkylation reactor at a lower investment cost. More importantly, the ethylene yield is higher than the original feed ethylene content and, thus, the ethylbenzene production rate is markedly increased by as much as 1.7 times. These results are significant and unexpected.

A means for removing paraffins and olefins can be placed between D and A to concentrate the ethylene further. The ethane thus removed can be sent to the cracker for dehydrogenation. Concentrating the stream in this manner would allow for a liquid phase alkylation reaction. The means for removing the ethane can be a fractionation column using a refrigerant, an adsorption-desorption device such as a pressure swing adsorption unit or a membrane-based separation unit. Also, it is possible to place the paraffin/olefin separation unit downstream of the heavy olefins removal unit (A).

Example 3

Figure 3:
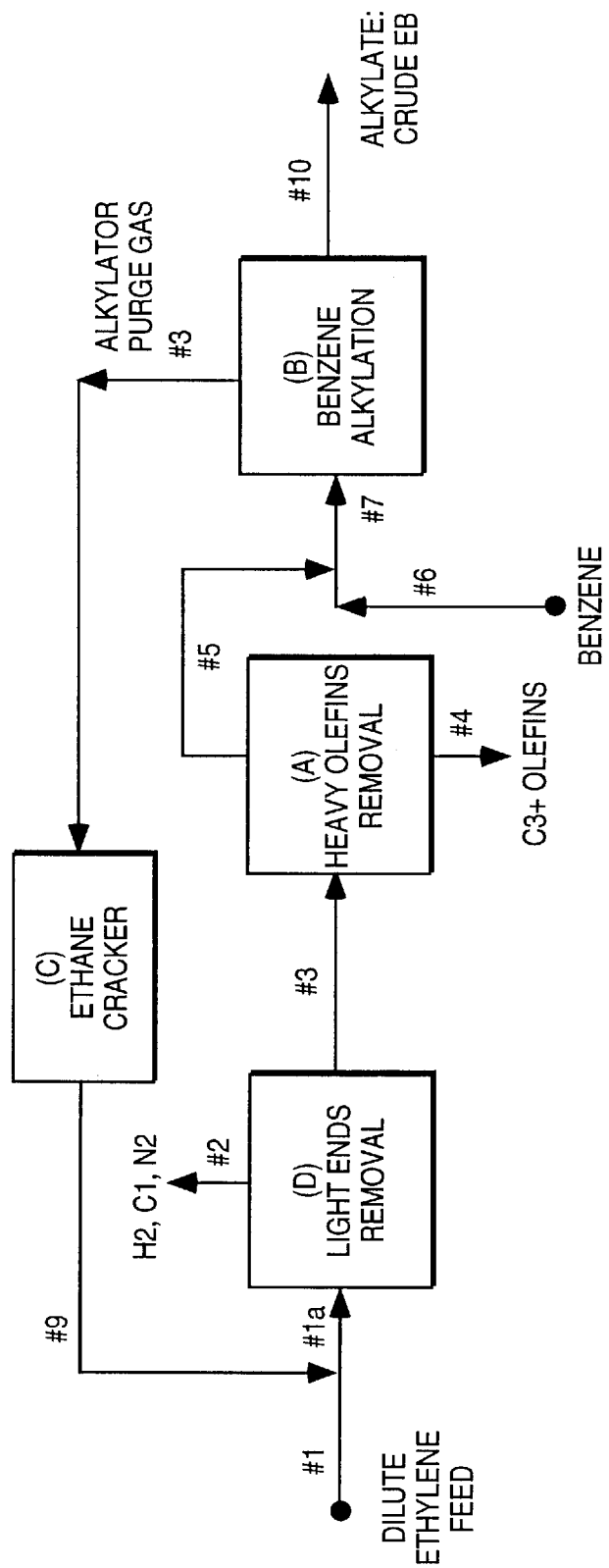
FIG. 3 illustrates an embodiment of the invention which is the same as that shown in FIG. 2 with the exception that the light ends removal facility D is a pressure swing adsorption unit.
Figure 4:
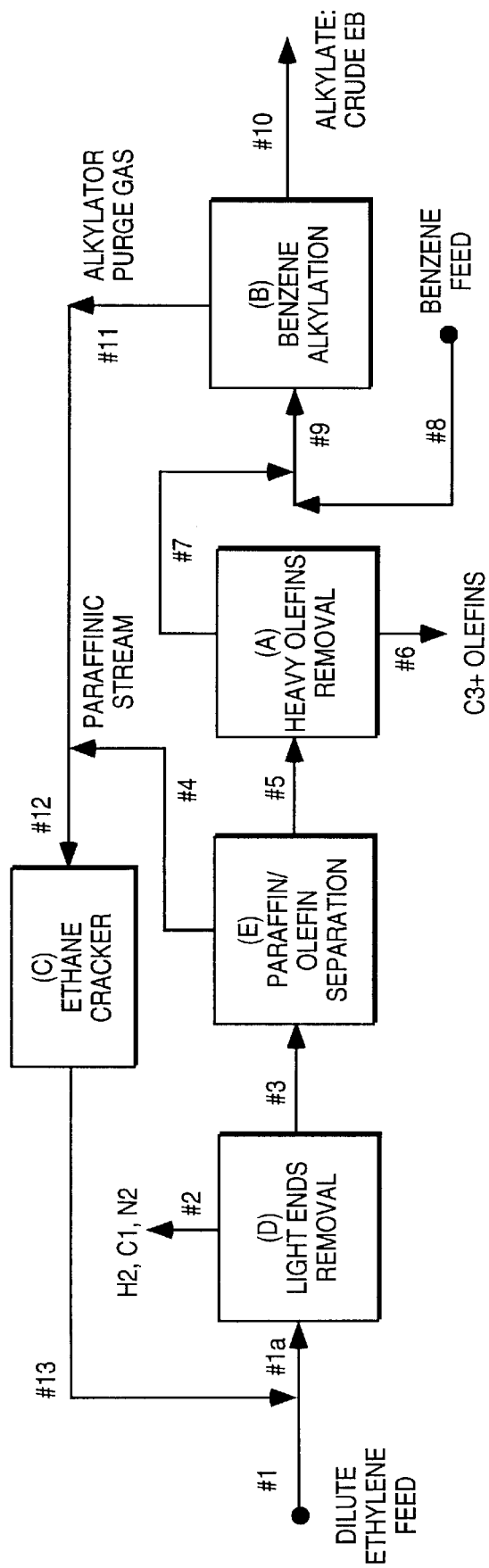
FIG. 4 illustrates an embodiment of the invention in which a paraffin/olefin separation unit (E) is incorporated into the process illustrated in FIG. 2 or FIG. 3.

The embodiment of Example 3 is identical to Example 2, except that a pressure swing adsorption (PSA) unit is used in place of the demethanizer of the previous example for removing light ends, D. The process schematic diagram, which is identical to FIG. 2, is displayed again in FIG. 3. But, the material balance given in Table III is somewhat different from Table II of Example 2.

A PSA unit is a class of separation equipment consisting of a single or multiple bed of solid adsorbents operated cyclically between adsorption and desorption modes to achieve desired separation, and has a wide range of commercial applications including high purity (99.99%) hydrogen production from light hydrocarbon mixtures. *Pressure Swing Adsorption* by D. M. Ruthven, S. Farooq, K. S. Knaebel, VCH Publishers, Inc., 1994, describes Pressure Swing Adsorption technology.

A PSA unit is used in this example because it is a non-cryogenic separation apparatus which has the advantages of being much less expensive to install and operate than a demethanizer column although the separation efficiencies may be somewhat lower. For this example, the hydrogen and methane recovery rates from D are taken respectively as 90% and 75% instead of the 99% for both components of Example 2. In addition, 8% of incoming ethylene in the combined stream #1a is lost to the light ends product stream #2, as compared to 2% loss in Example 2.

One may install another PSA unit to further process the light ends stream 2 to recover high purity hydrogen and be able to recycle ethylene back to stream 1a, thereby minimizing ethylene loss to the light ends fuel gas stream. This sort of feature is also an embodiment of the present invention.

The material balance given in Table III, as calculated according to standard engineering practices, shows that the ethylene produced for the alkylation reaction, i.e., stream 5, exceeds the amount of ethylene contained in the original dilute ethylene feed stream 1 by 151.5 wt. %. Thus, the ethylbenzene production is increased by 155% (i.e., 151.5/98×100) relative to the embodiment of Example 1. The process of this Example 3 has an additional advantage in that it produces a substantially smaller volumetric flow to the alkylation reactor with much higher ethylene concentrations relative to the process of Example 1. As a result, per pound of EB production capacity, the alkylation reactor can be smaller.

The major results of Examples 1–3 are summarized in Table B.

Also, while the volume of light ends to be disposed of as fuel gas is about the same magnitude for all three examples, the light ends in Examples 2 and 3 contain more hydrogen than in Example 1. This hydrogen may be recovered as a valuable by-product.

TABLE B

Comparison of Benefits

|  | Example 1 | Example 2 | Example 3 |
|---|---|---|---|
| Dilute Ethylene Feed |  |  |  |
| Ethylene content (lb/hr) | 13,000 | 13,000 | 13,000 |
| Total vol. flow (MMSCFD) | 25.8 | 25.8 | 25.8 |
| Alkylation Reactor Feed Gas |  |  |  |
| Total gas flow (MMSCFD) | 24.7 | 13.2 | 16.1 |
| Ethylene conc. (Mole %) | 16.8 | 53.8 | 39.7 |
| Ethylene flow (lb/hr) | 12,740 | 21,888 | 19,689 |
| Ethylene yield on Feed $C_2=$ | 98.0% | 168.4% | 151.5% |
| Ethylbenzene Production (lb/hr) | 47,748 | 82,034 | 73,792 |
| Relative production rate | 1.0 | 1.72 | 1.55 |
| By-product Fuel Gas (MMSCFD) | 20.5 | 21.1 | 21.5 |

Example 4

The embodiment of Example 4 is identical to that described in Example 3, except that a paraffin/olefin separation unit (E) is installed between the light ends removal facility (D) and the heavy olefins removal unit (A) in order to reject paraffins as a waste stream #4 and thereby increase the ethylene concentration further in the stream (#7) leading to the alkylation reactor. The material balance for Example 4, as calculated according to standard engineering practices, is given in Table IV.

The facility E can be a PSA unit or a membrane based separation unit. For this particular example, a PSA unit is employed. Its separation performance is such that 55 mole percent of ethane is rejected to stream #4 while ethylene recovered in its product stream #5 is 88 mole percent. Other hydrocarbon components would have different separation factors. The paraffin/olefin separation unit (E), which in this case is a PSA unit, is operated using conditions which will minimize the ethylene loss to stream #4 while removing a substantial amount of ethane and other paraffinic components.

In another embodiment of the invention, the positions of the paraffin/olefin separation unit (E) and the heavy olefins removal unit (A) may be switched so that the paraffin/olefin separation unit (E) is placed downstream of the heavy olefins removal unit (A).

The benefits of the process embodied in Example 4 are evident when the amount of ethylene in stream #7 going to the alkylation reactor, shown in Table IV, is compared with that of the ethylene stream #3 going to the alkylation reactor of Example 1, shown in Table I.

Table IV shows that in utilizing the identical dilute ethylene feed stream #1, the process of Example 4 results in a much smaller volumetric flow rate to the alkylation reactor, 9.0 MMSCFD for Example 4 vs. 24.7 MMSCFD for Example 1, with a substantially higher ethylene concentration, 70.5 mole % for Example 4 vs. 16.8 mole % for Example 1.

TABLE I

| Stream # | 1 Dilute Ethylene Feed | | | 2 Heavy Olefins | | 3 Alkylation Reactor Feed Gas | | | 6 Purge Gas From Alkylation Section | | |
|---|---|---|---|---|---|---|---|---|---|---|---|
| Component | lb/hr | wt % | mol % | lb/hr | wt % | lb/hr | mol % | wt % | lb/hr | mol % | wt % |
| Hydrogen | 1,250 | 2.30 | 22.08 | 0 | — | 1,250 | 23.08 | 2.56 | 1,250 | 27.75 | 3.46 |
| $N_2$ & $CO_2$ | 5,160 | 9.50 | 6.10 | 0 | — | 5,160 | 6.37 | 10.57 | 5,160 | 7.66 | 14.30 |
| Methane | 16,000 | 29.45 | 35.33 | 0 | — | 16,000 | 36.93 | 32.76 | 16,000 | 44.40 | 44.35 |
| Ethane | 13,750 | 25.31 | 16.19 | 137 | 2.50 | 13,613 | 16.76 | 27.87 | 13,613 | 20.14 | 37.73 |
| Ethylene | 13,000 | 23.93 | 16.40 | 260 | 4.73 | 12,740 | 16.80 | 26.09 | 0 | 0.00 | 0.00 |
| Propane | 750 | 1.38 | 0.60 | 713 | 12.97 | 38 | 0.03 | 0.08 | 38 | 0.04 | 0.10 |
| Propylene | 2,650 | 4.88 | 2.23 | 2,637 | 47.98 | 13 | 0.012 | 0.027 | 0 | 0.00 | 0.00 |
| C4 Olefins | 780 | 1.44 | 0.49 | 776 | 14.12 | 4 | 0.003 | 0.008 | 0 | 0.00 | 0.00 |
| C4 Paraffins | 740 | 1.36 | 0.45 | 725 | 13.20 | 15 | 0.009 | 0.030 | 15 | 0.01 | 0.04 |
| C5+ | 250 | 0.46 | 0.12 | 248 | 4.50 | 2 | 0.001 | 0.005 | 2 | 0.001 | 0.01 |
| Total, lb/hr | 54,330 | 100.00 | 100.00 | 5,496 | 100.00 | 48,834 | 100.00 | 100.00 | 36,077 | 100.00 | 100.00 |
| MMSCF/Day | 25.8 | | | 1.1 | | 24.7 | | | 20.5 | | |
| Ethylene Produced for Alkylation: | | | | | | 12,740 | lb/hr | | Purge Gas as % of Stream #1 | | |
| Wt % Yield on Feed C2 = content: | | | | | | 98.0% | wt % | | 66.4% | by weight | |
| EB Produced by alkylation: | | | | | | 47,748 | lb/hr | | 79.6% | by volume | |

TABLE II

| Stream # | 1 Dilute Ethylene Feed | | 1a | 2 Light Ends By-Product | | 3 | | 4 Hvy Olefin |
|---|---|---|---|---|---|---|---|---|
| Component | lb/hr | mol % | lb/hr | lb/hr | mol % | lb/hr | wt % | lb/hr |
| Hydrogen | 1,250 | 22.08 | 2,117 | 2,096 | 45.32 | 21 | 0.04 | 0 |
| $N_2$ & $CO_2$ | 5,160 | 6.10 | 5,600 | 5,160 | 7.46 | 440 | 0.90 | 0 |
| Methane | 16,000 | 35.33 | 17,266 | 17,093 | 46.20 | 173 | 0.35 | 0 |
| Ethane | 13,750 | 16.19 | 19,477 | 195 | 0.28 | 19,282 | 39.27 | 193 |
| Ethylene | 13,000 | 16.40 | 22,791 | 456 | 0.70 | 22,335 | 45.49 | 447 |
| Propane | 750 | 0.60 | 803 | 4 | 0.00 | 799 | 1.63 | 759 |
| Propylene | 2,650 | 2.23 | 2,965 | 15 | 0.02 | 2,951 | 6.01 | 2,936 |
| C4 Olefins | 780 | 0.49 | 1,126 | 3 | 0.00 | 1,123 | 2.29 | 1,117 |
| C4 Paraffins | 740 | 0.45 | 766 | 2 | 0.00 | 764 | 1.56 | 749 |
| C5+ | 250 | 0.12 | 1,210 | 0 | 0.00 | 1,210 | 2.46 | 1,198 |
| Total, lb/hr | 54,330 | 100.00 | 74,120 | 25,023 | 100.00 | 49,097 | 100.00 | 7,398 |
| MMSCF/Day | 25.8 | | 35.7 | 21.1 | | 14.7 | | 1.4 |
| Ethylene Produced for Alkylation: | | | | | | | | |
| Wt % Yield on Feed C2 = content: | | | | | | | | |
| EB Produced by alkylation: | | | | | | | | |

| Stream # | 5 Alkylation Reactor Feed Gas | | | 8 Purge Gas From Alky | | 9 Cracker Effluent | |
|---|---|---|---|---|---|---|---|
| Component | lb/hr | mol % | wt % | lb/hr. | wt % | lb/hr | wt % |
| Hydrogen | 21 | 0.73 | 0.05 | 21 | 0.11 | 867 | 4.38 |
| $N_2$ & $CO_2$ | 440 | 0.74 | 1.05 | 440 | 2.22 | 440 | 2.22 |
| Methane | 173 | 0.74 | 0.41 | 173 | 0.87 | 1,266 | 6.40 |
| Ethane | 19,089 | 43.83 | 45.78 | 19,089 | 96.46 | 5,727 | 28.94 |

TABLE II-continued

| | | | | | | |
|---|---|---|---|---|---|---|
| Ethylene | 21,888 | 53.84 | 52.49 | 0 | 0.00 | 9,791 | 49.47 |
| Propane | 40 | 0.06 | 0.10 | 40 | 0.20 | 53 | 0.27 |
| Propylene | 15 | 0.024 | 0.035 | 0 | 0.00 | 315 | 1.59 |
| C4 Olefins | 6 | 0.007 | 0.013 | 0 | 0.00 | 346 | 1.75 |
| C4 Paraffins | 15 | 0.018 | 0.037 | 15 | 0.08 | 26 | 0.13 |
| C5+ | 12 | 0.010 | 0.029 | 12 | 0.06 | 960 | 4.85 |
| Total, lb/hr | 41,699 | 100.00 | 100.00 | 19,790 | 100.00 | 19,790 | 100.00 |
| MMSCF/Day | 13.2 | | | 6.1 | | 9.9 | |
| Ethylene Produced for Alkylation: | 21,888 | lb/hr | | C2 = produced | | 75.3% on #1 C2 = | |
| Wt % Yield on Feed C2= content: | 168.4% | wt % | | C2 Conv.: | | 70.0 | wt % |
| EB Produced by alkylation: | 82,034 | lb/hr | | C2 = Select.: | | 73.3 | wt % |
| | | M % C/S | | 70.00 | | 78.50 | |

TABLE III

| Stream # | 1 Dilute Ethylene Feed | | 1a | 2 Light Ends By-Product | | 3 | | 4 Hvy Olefin |
|---|---|---|---|---|---|---|---|---|
| Component | lb/hr | mol % | lb/hr | lb/hr | mol % | lb/hr | wt % | lb/hr |
| Hydrogen | 1,250 | 22.08 | 2,237 | 2,014 | 42.59 | 224 | 0.44 | 0 |
| N₂ & CO₂ etc | 5,160 | 6.10 | 6,055 | 5,160 | 7.30 | 895 | 1.77 | 0 |
| Methane | 16,000 | 35.33 | 22,649 | 16,987 | 44.91 | 5,662 | 11.21 | 0 |
| Ethane | 13,750 | 16.19 | 18,920 | 1,514 | 2.13 | 17,406 | 34.47 | 174 |
| Ethylene | 13,000 | 16.40 | 21,838 | 1,747 | 2.64 | 20,091 | 39.79 | 402 |
| Propane | 750 | 0.60 | 799 | 64 | 0.06 | 735 | 1.46 | 698 |
| Propylene | 2,650 | 2.23 | 2,935 | 235 | 0.24 | 2,700 | 5.35 | 2,686 |
| C4 Olefins | 780 | 0.49 | 1,092 | 76 | 0.06 | 1,016 | 2.01 | 1,011 |
| C4 Paraffins | 740 | 0.45 | 764 | 60 | 0.04 | 704 | 1.39 | 690 |
| C5+ | 250 | 0.12 | 1,116 | 58 | 0.03 | 1,058 | 2.10 | 1,048 |
| Total, lb/hr | 54,330 | 100.30 | 78,404 | 27,913 | 100.00 | 50,491 | 100.00 | 6,709 |
| MMSCF/Day | 25.8 | | 39.0 | 21.5 | | 17.4 | | 1.3 |
| Ethylene Produced for Alkylation: | | | | | | | | |
| Wt % Yield on Feed C2 = content: | | | | | | | | |
| EB Produced by alkylation: | | | | | | | | |

| Stream # | 5 Alkylation Reactor Feed Gas | | | 8 Purge Gas From Alky | | 9 Cracker Effluent | |
|---|---|---|---|---|---|---|---|
| Component | lb/hr | mol % | wt % | lb/hr. | wt % | lb/hr | wt % |
| Hydrogen | 224 | 6.31 | 0.51 | 224 | 0.93 | 987 | 4.10 |
| N₂ & CO₂ etc | 895 | 1.52 | 2.04 | 895 | 3.72 | 895 | 3.72 |
| Methane | 5,662 | 19.97 | 12.93 | 5,662 | 23.52 | 6,649 | 27.62 |
| Ethane | 17,232 | 32.42 | 39.36 | 17,232 | 71.58 | 5,170 | 21.47 |
| Ethylene | 19,689 | 39.69 | 44.97 | 0 | 0.00 | 8,838 | 36.71 |
| Propane | 37 | 0.05 | 0.08 | 37 | 0.15 | 49 | 0.20 |
| Propylene | 13 | 0.018 | 0.031 | 0 | 0.00 | 285 | 1.18 |
| C4 Olefins | 5 | 0.005 | 0.012 | 0 | 0.00 | 312 | 1.30 |
| C4 Paraffins | 14 | 0.014 | 0.032 | 14 | 0.06 | 24 | 0.10 |
| C5+ | 11 | 0.007 | 0.024 | 11 | 0.04 | 866 | 3.60 |
| Total, lb/hr | 43,782 | 100.00 | 100.00 | 24,074 | 100.00 | 24,074 | 100.00 |
| MMSCF/Day | 16.1 | | | 9.7 | | 13.2 | |
| | 19,689 | lb/hr | | C2 = produced | | 68.0% on #1 C2= | |
| | 151.5% | wt % | | C2 Conv.: | | 70.0 | wt % |
| | 73,792 | lb/hr | | C2 = Select.: | | 73.3 | wt % |
| | | | | M % C/S | | 70.00 | 78.50 |

TABLE IV

| Stream # | 1 Dilute Ethylene Feed | | 1a | 2 Lt. Ends | 3 | 4 Paraffin separated | | 5 | 6 Hvy Olefin |
|---|---|---|---|---|---|---|---|---|---|
| Component | lb/hr | mol % | lb/hr | lb/hr | lb/hr | lb/hr | wt % | lb/hr | lb/hr |
| Hydrogen | 1,250 | 22.08 | 2,244 | 2,019 | 224 | 213 | 0.71 | 11 | 0 |
| N₂,CO₂,etc | 5,160 | 6.10 | 6,055 | 5,160 | 895 | 850 | 2.83 | 45 | 0 |
| Methane | 16,000 | 35.33 | 22,659 | 16,994 | 5,665 | 5,268 | 17.55 | 397 | 0 |

TABLE IV-continued

| | | | | | | | | | |
|---|---|---|---|---|---|---|---|---|---|
| Ethane | 13,750 | 16.19 | 18,959 | 1,517 | 17,442 | 9,593 | 31.96 | 7,849 | 78 |
| Ethylene | 13,000 | 16.40 | 24,624 | 1,970 | 22,654 | 2,719 | 9.06 | 19,936 | 399 |
| Propane | 750 | 0.60 | 1,525 | 122 | 1,403 | 730 | 2.43 | 674 | 640 |
| Propylene | 2,650 | 2.23 | 5,439 | 435 | 5,004 | 2,502 | 8.33 | 2,502 | 2,489 |
| C4 Olefins | 780 | 0.49 | 3,856 | 270 | 3,586 | 2,761 | 9.20 | 825 | 821 |
| C4 Paraffins | 740 | 0.45 | 2,623 | 205 | 2,419 | 1,883 | 6.20 | 556 | 545 |
| C5+ | 250 | 0.12 | 4,644 | 241 | 4,403 | 3,523 | 11.73 | 881 | 872 |
| Total, lb/hr | 54,330 | 100.0 | 92,628 | 28,932 | 63,696 | 30,021 | 100.0 | 33,675 | 5,844 |
| MMSCFD | 25.8 | | 41.7 | 21.8 | 20.0 | 9.8 | | 10.2 | 1.1 |

Ethylene Produced for Alkylation, lb/hr:
Wt % Yield on #1 Feed C2 = content:
EB Produced by alkylation, lb/hr:

| | 7 | | 11 | | 13 | |
|---|---|---|---|---|---|---|
| Stream # | Alky. Reactor feed gas | | Purge gas from Alky | | Cracker Effluent | |
| Component | lb/hr | mol % | lb/hr | wt % | lb/hr | wt % |
| Hydrogen | 11 | 0.57 | 11 | 0.14 | 994 | 2.59 |
| N$_2$,CO$_2$,etc | 45 | 0.13 | 45 | 0.55 | 895 | 2.34 |
| Methane | 397 | 2.50 | 397 | 4.79 | 6,659 | 17.39 |
| Ethane | 7,771 | 26.17 | 7,771 | 93.88 | 5,209 | 13.60 |
| Ethylene | 19,537 | 70.49 | 0 | 0.00 | 11,624 | 30.35 |
| Propane | 34 | 0.077 | 34 | 0.41 | 775 | 2.02 |
| Propylene | 13 | 0.030 | 0 | 0.00 | 2,789 | 7.28 |
| C4 Olefins | 4 | 0.008 | 0 | 0.00 | 3,076 | 8.03 |
| C4 Paraffins | 11 | 0.019 | 11 | 0.13 | 1,883 | 4.92 |
| C5+ | 9 | 0.011 | 9 | 0.11 | 4,394 | 11.47 |
| Total, lb/hr | 27,831 | 100.0 | 8,277 | 100.0 | 38,298 | 100.0 |
| MMSCFD | 9.0 | | 2.7 | | 16.0 | |
| | 19,537 | | C2 Conv.: | | 70.0 | wt % |
| | 150.3% | | C2 = Select.: | | 73.3 | wt % |
| | 73,222 | | | | | |

That which is claimed is:

1. A process for producing ethylbenzene from an ethylene stream comprising a dilute ethylene stream from a fluid catalytic cracking (FCC) operation and an effluent stream from dehydrogenation of ethane in a thermal steam cracker, said ethylene stream containing a light ends component comprising hydrogen and methane and a heavy cut comprising ethylene, ethane, and C$_3$+ hydrocarbons, which process comprises:

(a) separating the light ends from the heavy cut by passing the dilute ethylene stream through a light ends removal unit and recovering an effluent stream comprising said light ends and another effluent stream containing said heavy cut;

(b) separating the C$_3$+ hydrocarbons from the heavy cut by passing the effluent stream containing the heavy cut from the light ends removal unit through a heavy olefins removal unit under pressure and temperature conditions sufficient to separate substantially all of the C$_3$+ hydrocarbons and recovering an enriched ethylene effluent stream comprising ethylene and ethane;

(c) contacting the enriched ethylene effluent stream from the heavy olefins removal unit with benzene in the presence of an alkylation catalyst selected from aluminum chloride catalysts and zeolite catalysts in a reaction zone under reaction conditions wherein the benzene is alkylated by substantially all of the ethylene to form ethylbenzene and recovering the ethylbenzene;

(d) recovering from the reaction zone an alkylation reactor effluent stream comprising ethane;

(e) dehydrogenating at least a portion of the ethane in said alkylation reactor effluent stream in a thermal steam cracker to form an effluent stream containing ethylene; and (f) combining the ethylene-containing effluent stream thus formed with the dilute ethylene stream from the fluid catalytic cracking (FCC) operation going to the light ends removal unit thereby enriching the ethylene content of the dilute ethylene stream from the fluid catalytic cracking (FCC) operation and recycling to the reaction zone the ethylene formed by dehydrogenation.

2. The process of claim 1, wherein in step (a) the light ends removal unit is selected from a demethanizer, a pressure swing adsorption unit, and a membrane based separation unit having at least one bed of adsorbent.

3. The process of claim 2 wherein in step (a) the light ends removal unit is a pressure swing adsorption unit.

4. The process of claim 3 wherein the pressure swing adsorption unit has at least three beds of adsorbent.

5. The process of claim 4 wherein said adsorbent is selected from the group consisting of activated carbons, charcoal, silica gels, molecular sieves, activated clays, and activated aluminas.

6. The process of claim 3 wherein the effluent stream containing said heavy cut obtained following pressure swing adsorption in step (a) has an ethylene content of at least about 50 mole % of the ethylene content of the dilute ethylene stream entering the pressure swing adsorption unit.

7. The process of claim 6 wherein the effluent stream containing said heavy cut obtained following pressure swing adsorption in step (a) has an ethylene content of from about 80 mole % to about 98 mole % of the ethylene content of the dilute ethylene stream entering the pressure swing adsorption unit.

8. The process of claim 1 wherein in step (b) the heavy olefins removal unit is selected from a deethanizer and a sponge absorber equipped with a lean oil regeneration column.

9. The process of claim 1 wherein hydrogen is separated from the light ends effluent stream produced in step (a) and the hydrogen is recovered.

10. The process of claim 1 wherein the effluent stream containing said heavy cut obtained following light ends removal in step (a) has an ethylene content of at least about 50 mole % of the ethylene content of the dilute ethylene stream entering the light ends removal unit.

11. The process of claim 10 wherein the effluent stream containing said heavy cut obtained following light ends removal in step (a) has an ethylene content of from about 80 mole % to about 98 mole % of the ethylene content of the dilute ethylene stream entering the light ends removal unit.

12. The process of claim 1 wherein the concentration of ethylene in the enriched ethylene effluent stream contacted with benzene in step (c) is at least about 10 weight percent greater than the ethylene concentration of the dilute ethylene stream containing a light ends component and a heavy cut.

13. The process of claim 1 wherein the concentration of ethylene in the enriched ethylene effluent stream contacted with benzene in step (c) is from at least about 20 weight percent to about 60 weight percent greater than the ethylene concentration of the dilute ethylene stream containing a light ends component and a heavy cut.

14. The process of claim 1 wherein ethane is added to the alkylation reactor effluent stream prior to dehydrogenation.

15. The process of claim 1 wherein a means for separating paraffins from olefins is incorporated downstream of the light ends removal unit.

16. The process of claim 15 wherein the means for separating paraffins from olefins is selected from a pressure swing adsorption unit and a membrane based separation unit.

17. The process of claim 1 wherein a means for separating paraffins from olefins is incorporated downstream of the heavy olefins removal unit.

18. The process of claim 17 wherein the means for separating paraffins from olefins is selected from a pressure swing adsorption unit and a membrane based separation unit.

19. A process for producing ethylbenzene from an ethylene stream comprising a dilute ethylene stream from FCC offgas and an effluent stream from dehydrogenation of ethane in a thermal steam cracker, said ethylene stream containing a light ends component comprising hydrogen and methane and a heavy cut comprising ethylene, ethane, and $C_3+$ hydrocarbons, which process comprises:

(a) separating the light ends from the heavy cut by passing the dilute ethylene stream from FCC offgas to a pressure swing adsorption unit and contacting it with an adsorbent selective for the adsorption of said heavy cut under a pressure and temperature at which at least a portion of the heavy cut is adsorbed and recovering an effluent stream comprising said light ends and then desorbing said heavy cut from the adsorbent under reduced pressure and recovering another effluent stream containing said heavy cut;

(b) contacting the effluent stream containing the heavy cut with a deethanizer under a pressure and temperature sufficient to separate substantially all of the $C_3+$ hydrocarbons and recovering a dilute ethylene effluent stream comprising ethylene and ethane;

(c) contacting the dilute ethylene effluent stream from the deethanizer with benzene in the presence of an alkylation catalyst selected from aluminum chloride catalysts and zeolite catalysts in a reaction zone under reaction conditions wherein the benzene is alkylated by substantially all of the ethylene to form ethylbenzene and recovering the ethylbenzene;

(d) recovering from the reaction zone an alkylation reactor effluent stream comprising ethane;

(e) dehydrogenating at least a portion of the ethane in said alkylation reactor effluent stream in a thermal steam cracker to form an effluent stream containing ethylene; and (f) combining the ethylene-containing effluent stream thus formed with the dilute ethylene stream from FCC offgas going to the pressure swing adsorption unit thereby enriching the ethylene content of the FCC offgas stream and recycling to the reaction zone the ethylene formed by dehydrogenation.

20. The process of claim 19 wherein the pressure swing adsorption unit has at least three beds of adsorbent.

21. The process of claim 20 wherein said adsorbent is selected from the group consisting of activated carbon, charcoal, silica gel, or a zeolite molecular sieve.

22. The process of claim 19 wherein the light ends separated in step (a) are passed through a demethanizer to separate methane from hydrogen and the hydrogen is recovered.

23. The process of claim 19 wherein the effluent stream containing said heavy cut obtained following light ends removal in step (a) has an ethylene content of at least about 50 mole % of the ethylene content of the dilute ethylene stream entering the light ends removal unit.

24. The process of claim 23 wherein the effluent stream containing said heavy cut obtained following light ends removal in step (a) has an ethylene content of from about 80 mole % to about 98 mole % of the ethylene content of the dilute ethylene stream entering the light ends removal unit.

25. The process of claim 19 wherein the pressure swing adsorption unit has at least 10 beds of adsorbent.

26. The process of claim 19 wherein the concentration of ethylene in the dilute ethylene effluent stream contacted with benzene in step (c) is at least about 10 weight percent greater than the ethylene concentration of the dilute ethylene stream from FCC offgas.

27. The process of claim 19 wherein the concentration of ethylene in the dilute ethylene effluent stream contacted with benzene in step (c) is from at least about 20 weight percent to about 60 weight percent greater than the ethylene concentration of the dilute ethylene stream from FCC offgas.

28. A process for producing ethylbenzene from an ethylene stream comprising a dilute ethylene stream from FCC offgas and an effluent stream from dehydrogenation of ethane in a thermal steam cracker, said ethylene stream comprising hydrogen, methane, ethane, ethylene, and $C_3+$ hydrocarbons, said process comprising:

(a) subjecting said dilute ethylene stream to a cyclic adsorption process in at least one bed of adsorbent which selectively adsorbs ethylene, ethane, and $C_3+$ hydrocarbons, thereby producing a non-adsorbed hydrogen and methane component and an adsorbed ethylene, ethane, and $C_3+$ hydrocarbon component;

(b) removing the non-adsorbed hydrogen and methane component and optionally separating and recovering the hydrogen;

(c) desorbing the ethylene, ethane, and $C_3+$ hydrocarbon component and contacting it with a deethanizer under a pressure and temperature sufficient to separate substantially all of the $C_3+$ hydrocarbons and recovering a dilute ethylene effluent stream comprising ethylene and ethane;

(d) contacting the dilute ethylene effluent stream from the deethanizer with benzene in the presence of an alkylation catalyst selected from aluminum chloride catalysts and zeolite catalysts in a reaction zone under reaction conditions wherein the benzene is alkylated by substantially all of the ethylene to form ethylbenzene and recovering the ethylbenzene;

(e) recovering from the reaction zone an alkylation reactor effluent stream comprising ethane;

(f) dehydrogenating at least a portion of the ethane in said alkylation reactor effluent stream in a thermal steam cracker to form an effluent stream containing ethylene; and (g) combining the ethylene-containing effluent stream thus formed with the dilute ethylene stream from FCC offgas going to the bed of adsorbent in step (a) thereby enriching the ethylene content of the FCC offgas stream and recycling to the reaction zone the ethylene formed by dehydrogenation.

29. The process of claim 28 wherein at least three beds of absorbent are used in the cyclic adsorption process of step (a).

30. The process of claim 28 wherein said adsorbent is selected from the group consisting of activated carbon, charcoal, silica gel, or a zeolite molecular sieve.

31. The process of claim 28 wherein the ethylene, ethane, and $C_3+$ hydrocarbon component obtained following hydrogen and methane removal in step (b) has an ethylene content of at least about 50 mole % of the ethylene content of the dilute ethylene stream subjected to the cyclic adsorption process of step (a).

32. The process of claim 31 wherein the ethylene, ethane, and $C_3+$ hydrocarbon component obtained following hydrogen and methane removal in step (b) has an ethylene content of from about 80 mole % to about 98 mole % of the ethylene content of the dilute ethylene stream subjected to the cyclic adsorption process of step (a).

33. The process of claim 28 wherein the concentration of ethylene in the dilute ethylene effluent stream contacted with benzene in step (d) is at least about 10 weight percent greater than the ethylene concentration of the dilute ethylene stream from FCC offgas.

34. The process of claim 28 wherein the concentration of ethylene in the dilute ethylene effluent stream contacted with benzene in step (d) is from at least about 20 weight percent to about 60 weight percent greater than the ethylene concentration of the dilute ethylene stream from FCC offgas.

* * * * *

UNITED STATES PATENT AND TRADEMARK OFFICE
CERTIFICATE OF CORRECTION

PATENT NO.   : 5,856,607
DATED        : January 5, 1999
INVENTOR(S)  : Dae K. Kim It is certified that error appears in the above-identified patent and that said Letters Patent is hereby corrected as shown below:

Column 9,
Line 49, "include an suitable adsorbent" should read: -- include a suitable adsorbent --

Column 10,
Line 39, "3.5 kg/cm$^2$ to abut 28" should read: -- 3.5 kg/cm$^2$ to about 28 --
Line 50, "about 50 to abut 95" should read: -- about 50 to about 95 --

Column 13,
Line 48, "The purge gas form the alkylation" should read: -- "the purge gas from the alkylation --

Columns 21, 22
Table IV, [UNDER "Paraffin separated—1b/hr" COLUMN. LINE ENTITLED "C4 Paraffins' "1,883" should read: -- 1,863 --

UNITED STATES PATENT AND TRADEMARK OFFICE
CERTIFICATE OF CORRECTION

PATENT NO. : 5,856,607
DATED : January 5, 1999
INVENTOR(S) : Dae K. Kim

It is certified that error appears in the above-identified patent and that said Letters Patent is hereby corrected as shown below:

Title page,
In the title, "PROCESS FOR PRODUCTION OF ETHYLBENZENE FROME DILUTE ETHYLENE STREAMS" should read: -- "PROCESS FOR PRODUCTION OF ETHYLBENZENE FROM DILUTE ETHYLENE STREAMS"

Signed and Sealed this

Fourteenth Day of August, 2001

Attest:

NICHOLAS P. GODICI
Attesting Officer   Acting Director of the United States Patent and Trademark Office